United States Patent

Lang

[11] Patent Number: 6,102,897
[45] Date of Patent: Aug. 15, 2000

[54] MICROVALVE

[76] Inventor: Volker Lang, Zugspitzstrasse 52, 82131 Gauting, Germany

[21] Appl. No.: 09/101,951

[22] PCT Filed: Nov. 17, 1997

[86] PCT No.: PCT/EP97/06411

§ 371 Date: Sep. 15, 1998

§ 102(e) Date: Sep. 15, 1998

[87] PCT Pub. No.: WO98/22738

PCT Pub. Date: May 28, 1998

[30]     Foreign Application Priority Data

Nov. 19, 1996 [DE] Germany ............................ 196 47 838
Dec. 10, 1996 [DE] Germany ............................ 196 51 285
Jan. 23, 1997 [DE] Germany ............................ 197 02 361

[51] Int. Cl.$^7$ ............................................ A61M 5/80
[52] U.S. Cl. ................................ 604/246; 251/11; 137/67
[58] Field of Search .................................. 156/643, 644,
156/647, 653, 656, 657, 659.1, 662; 251/367,
368, 129.06, 11; 128/899; 604/890.1, 630,
93, 95, 246, 247; 600/573, 502; 137/67

[56]     References Cited

U.S. PATENT DOCUMENTS

| 1,734,186 | 11/1929 | Weidmann . | |
| 3,822,895 | 7/1974 | Ochiai . | |
| 4,267,853 | 5/1981 | Yamaguchi . | |
| 4,498,491 | 2/1985 | Chamberland . | |
| 5,238,223 | 8/1993 | Mettner et al. | 251/368 |
| 5,244,537 | 9/1993 | Ohnstein | 216/18 |
| 5,647,574 | 7/1997 | Mettner et al. | 251/129.06 |
| 5,681,024 | 10/1997 | Lisec et al. | 251/11 |
| 5,785,295 | 7/1998 | Tsai | 251/11 |
| 5,810,325 | 9/1998 | Carr | 251/30.02 |
| 5,819,749 | 10/1998 | Lee et al. | 128/899 |
| 5,865,417 | 2/1999 | Harris et al. | 251/11 |

*Primary Examiner*—Mark O. Polutta
*Assistant Examiner*—Jeremy Thissell
*Attorney, Agent, or Firm*—Ostrolenk, Faber, Gerb & Soffen, LLP

[57]     ABSTRACT

The invention relates to a microvalve for disposable use with a casing with at least one valve seat and a closing element fusible under thermal application for the opening and/or closing of the microvalve with electrical heating elements serving the thermal application being provided.

16 Claims, 8 Drawing Sheets

MICROVALVE

The invention relates to a microvalve for disposable use for use in analytical chemistry or medical technology and to one use of such a microvalve.

Particularly in the sector of intravenous infusion therapy and in medication applications, but also for diagnostic measures requiring the taking of blood samples, disposable systems are used almost exclusively for hygienic reasons. All active valves used here are still quite predominantly operated manually and are designed as three-way cocks singularly or multiply as cock valves. In addition, manually operable pinch clamps are still used as valves. Only in the sector of heart-lung machines and dialysers are sophisticated electromechanical valves used; however almost exclusively designed as hose pinch valves. It would therefore be desirable from the point of view of the physician, nurse or of hygiene to replace these labour-intensive manipulations which encourage operating errors with an automated valve control also for infusion therapy and diagnostic measures. However, this requires the possibility of using special very cost-favourable, electrically controllable valves.

The object of the invention described below was to provide simple, safe, cheap, small valves with a low dead spot which can be triggered electrically for analytical chemistry, but particularly for medical technology and here in particular for infusion therapy.

In accordance with the invention, this object is solved by means of a microvalve for disposable use with a casing with at least one valve seat and a closing element which fuses under the application of heat to open and/or close the microvalve with electrical heating elements to serve the heat application being provided.

In accordance with the invention, a microvalve is provided here with sample means which can be opened or closed once as required by the application of electrical energy.

Preferred embodiments of the microvalve in accordance with the invention are produced by the dependent claims following on from the main claim. Particularly advantageous is the use of a microvalve in accordance with the invention in an automatic, programmable infusion medication application apparatus.

Details and advantages of the invention are shown by means of the embodiments presented in the drawing.

Figure 13:
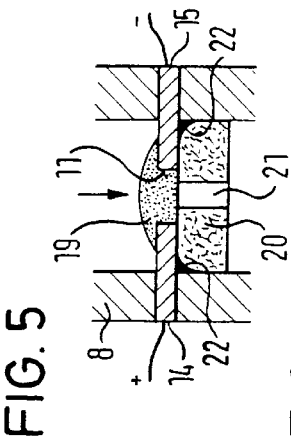
Figure 14:
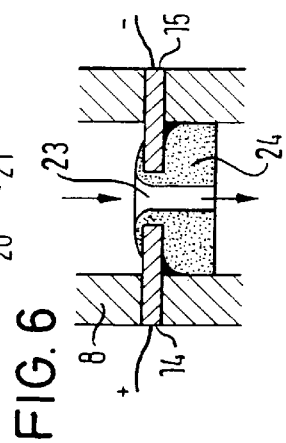

FIG. 13 and FIG. 14 finally show as an example another microvalve as an opener where the electrical resistance element is fitted directly to the easily thermally fusible valve closing membrane together with the electrical connection leads.

Figure 15:
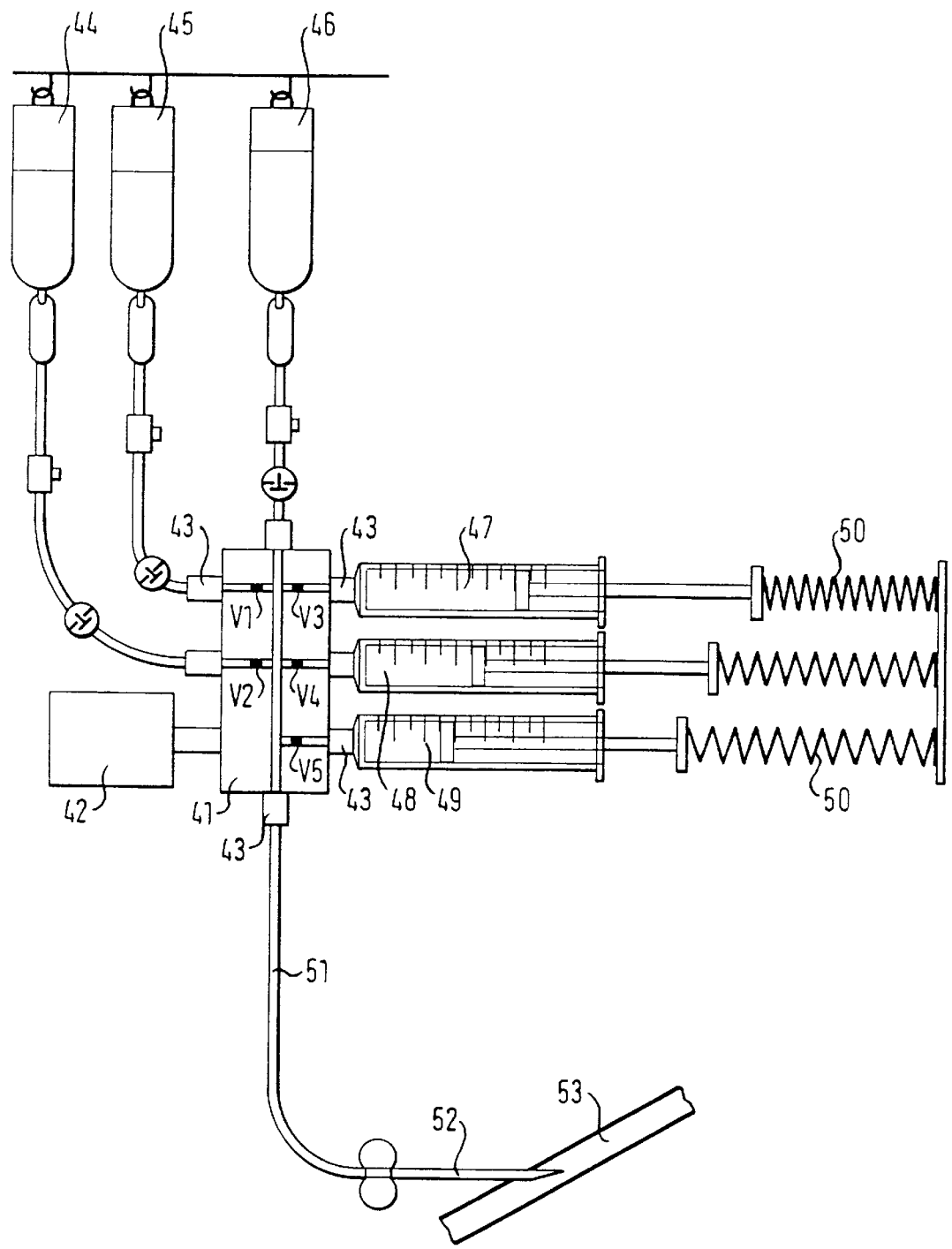

FIG. 15 shows as an application example from medical technology for disposable microvalves a programmable infusion medication application apparatus in a schematic view.

Figure 16:
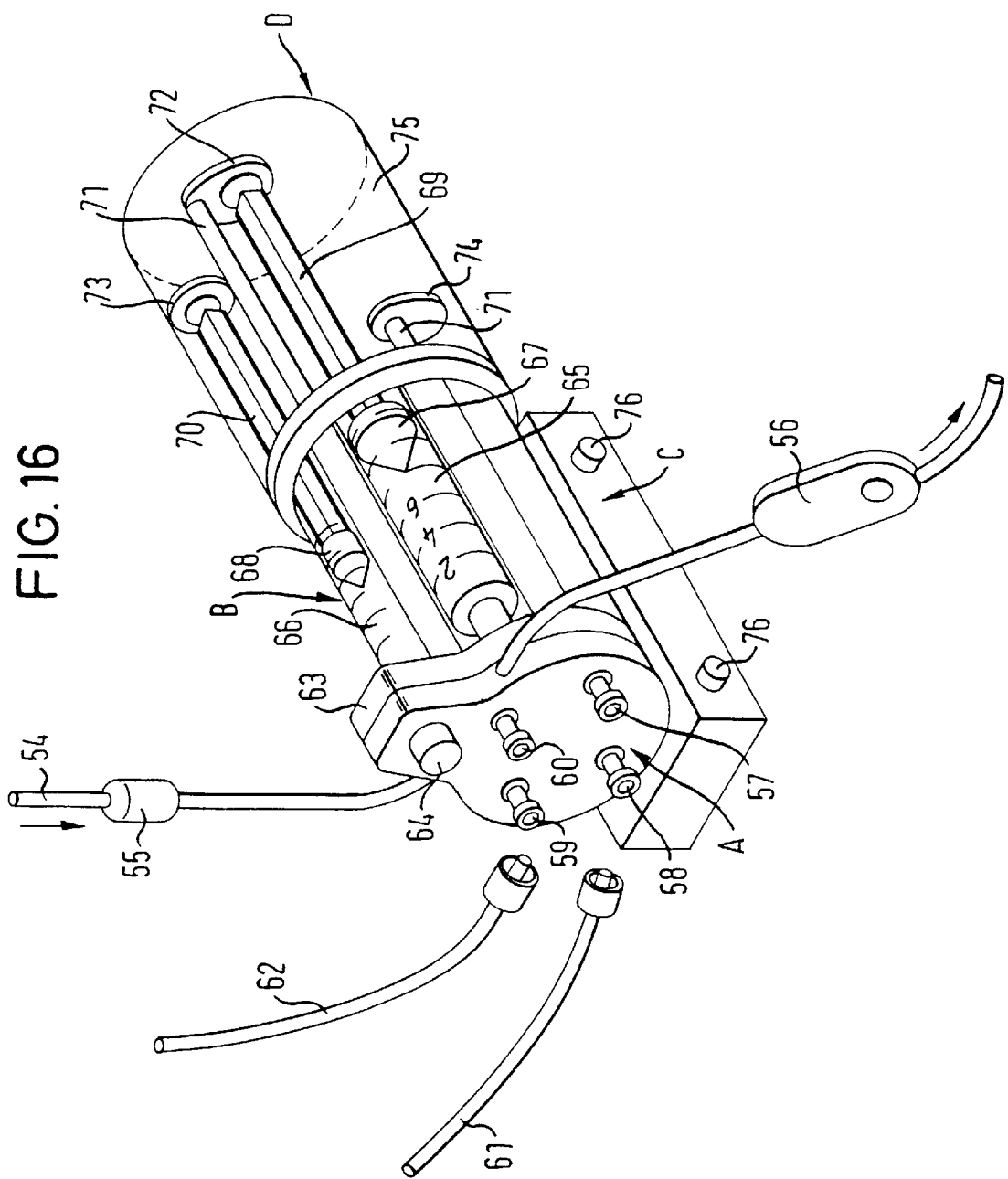

FIG. 16 shows in perspective view the infusion medication application apparatus with Parts A for disposable use and B, C and D for multiple use.

Figure 17:
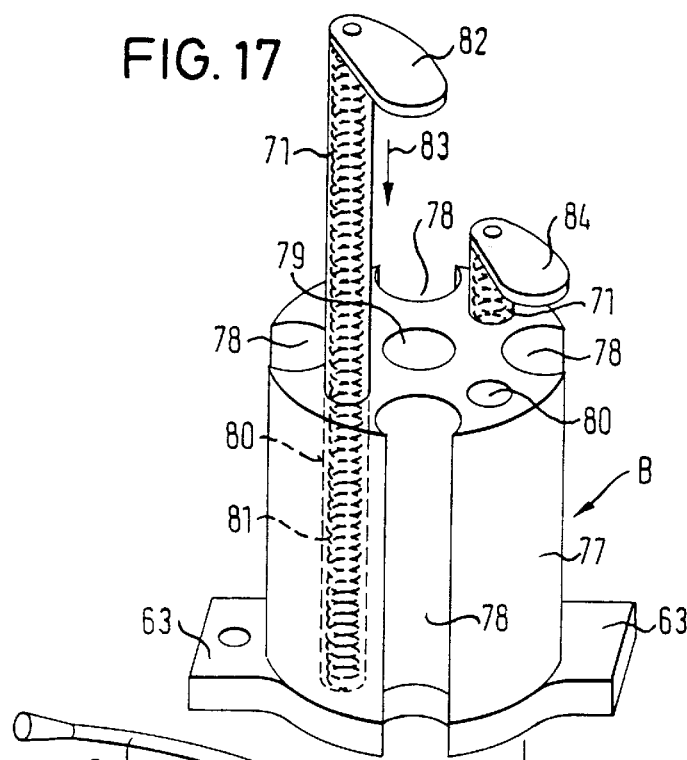

FIG. 17 shows in perspective view Part B, the syringe holding apparatus with spring transmission elements.

Figure 18:
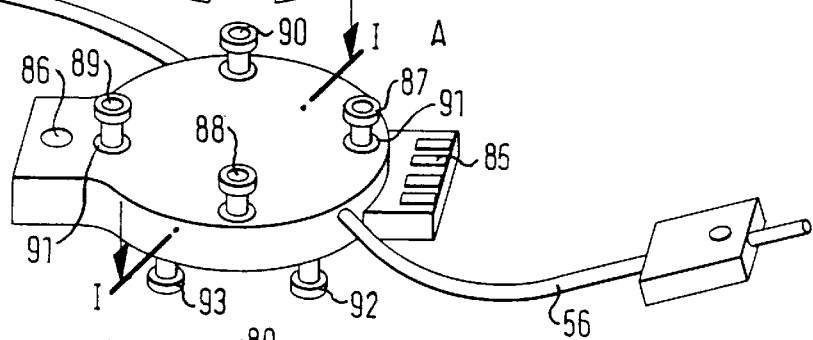

FIG. 18 shows in perspective view Part A, the electrically controlled valve metering distribution cartridge with Luer lock connections for hypodermic syringes, infusion containers and infusion pumps.

Figure 19:
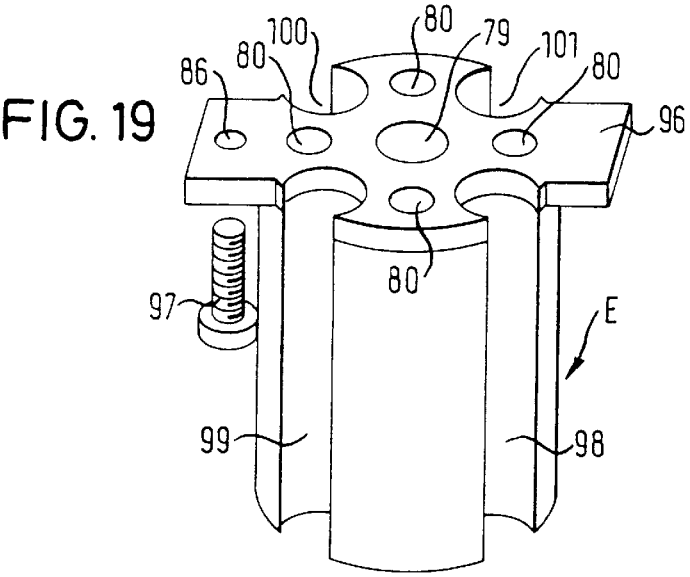

FIG. 19 shows in perspective view Part E, a syringe holding apparatus with spring transmission elements (not shown) which can additionally be connected to Part A.

FIG. 20 to FIG. 26 show in perspective view the components from which Part A is assembled.

Figure 27:
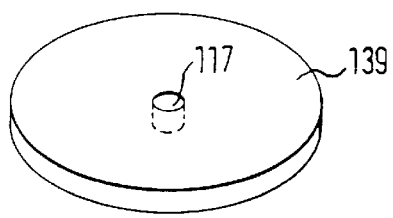
Figure 28:
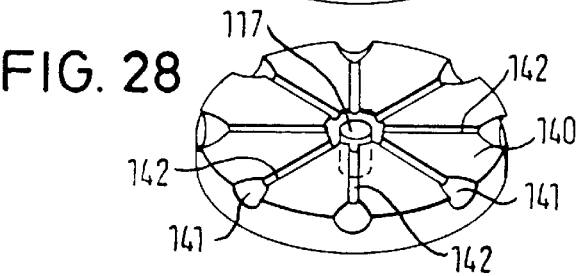

In FIG. 27 and FIG. 28, the metering apparatus made up of two parts taken out of Part A is also shown.

FIG. 27 shows in perspective view its plane top plate,

FIG. 28 its plane bottom plate provided with dosage grooves.

Figure 29:
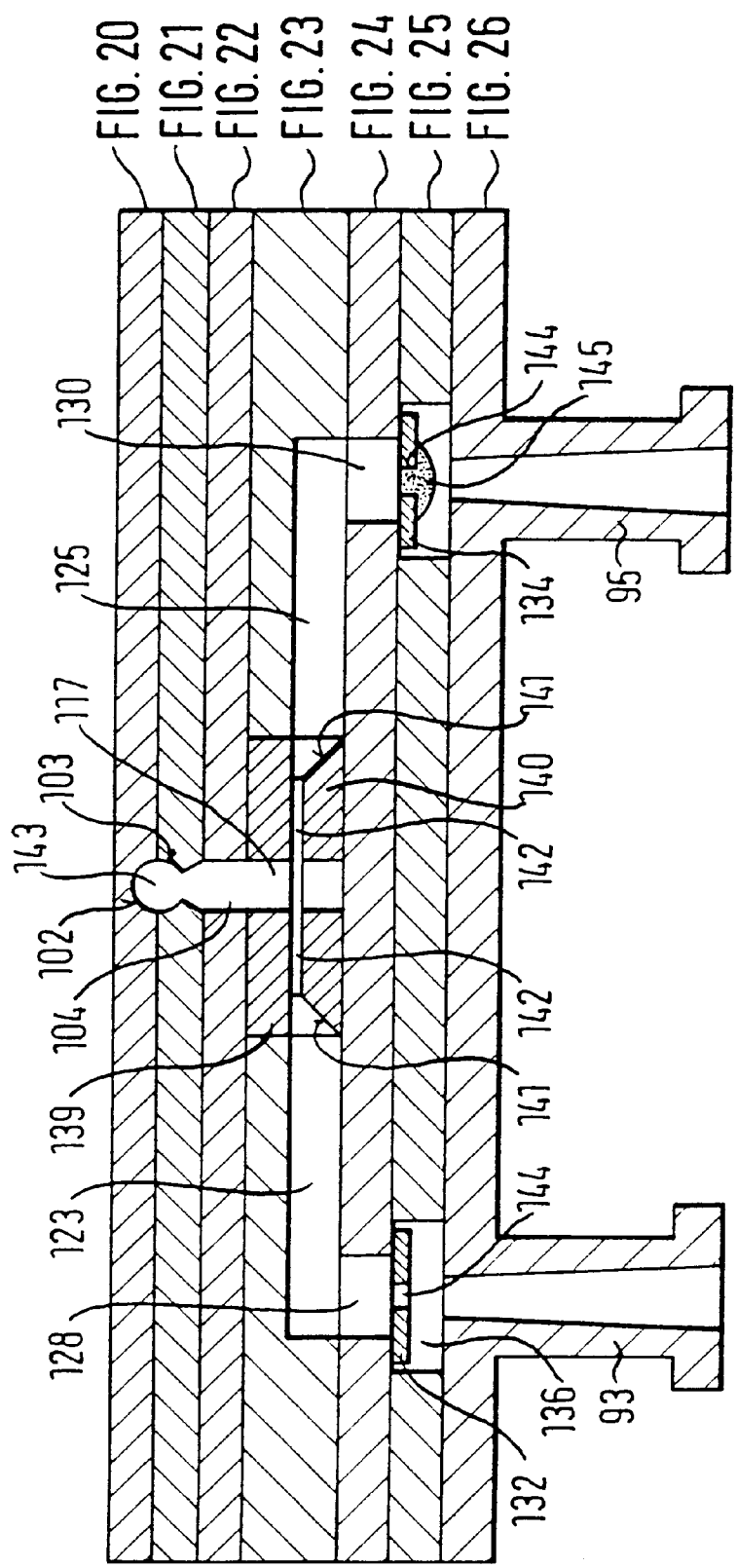

FIG. 29 shows in section Part A (section plane I . . . I, FIG. 3).

The valves in accordance with the invention are described below by means of FIGS. 1–14 and their use demonstrated for the example of an infusion medication application apparatus realised with them (FIG. 15 to FIG. 29).

Description of the electrical disposable microvalves

Figure 1:
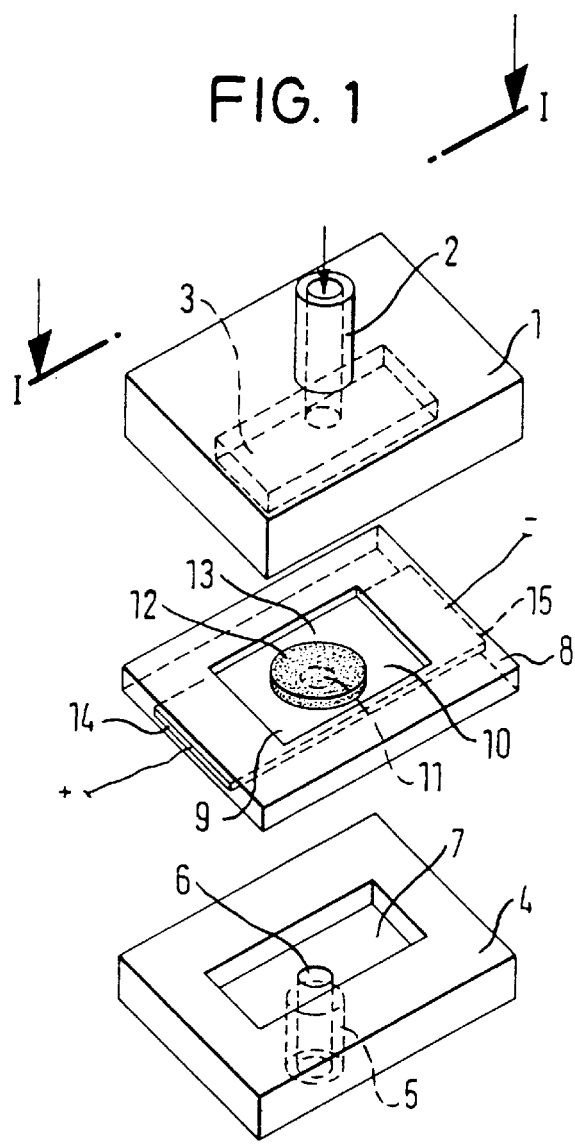
FIG. 1 shows as exploded drawing one simple embodiment of the electrical disposable microvalve.

FIG. 1 shows in an exploded drawing one simple embodiment of an electrical disposable microvalve with the function of an opener. It is tightly assembled from a valve casing upper part 1 drawn in transparent form with inlet nozzle 2, an inlet chamber 3 and a valve casing bottom part 4 with outlet nozzle 5, an outlet aperture 6 and the outlet chamber 7 with the valve support plate 8 being positioned therebetween. A perforated, rectangular PTC resistor plate in SMD design 10 (PTC resistor=an electrical positive temperature coefficient resistor) is cast or glued in a gas-tight manner into the valve support plate 8 with its rectangular cut out 9 in such a way that its perforation or valve aperture 11 (shown by a broken line as covered by the fusible closing plug 12) remains uncovered by plastic or glue in a wide seam 13 at the upper and lower side. However, in this way, the additional tight application of closures and special membranes also becomes possible without problem. The still required electrical contacting of the PTC plate can be performed very easily by means of the contacting strips 14, 15.

Figure 2:
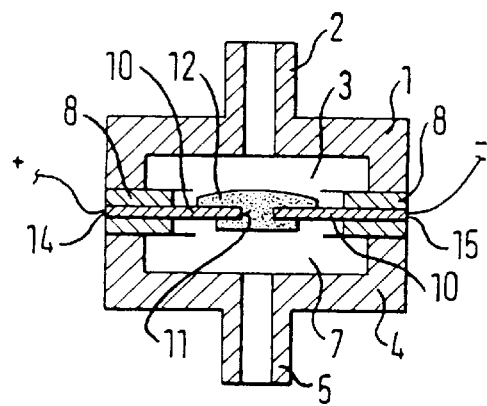
FIG. 2 shows the electrical disposable microvalve of FIG. 1 in section (section plane I . . . I).

FIG. 2 shows the assembled apparatus of FIG. 1 in section (section plane I . . . I). As can be seen, the valve casing upper part 1, with inlet nozzle 2 and an inlet chamber 3, is in a tight and gas-tight manner connected to the valve casing lower part 4 and its outlet nozzle 5 and the outlet chamber 7 via the valve support plate 8. The rectangular PTC resistor plate 10 with its perforation (valve aperture) 11, which is closed by the thermally fusible closing plug 12, is glued or cast in a gas-tight manner into the frame of the valve support plate 8. The required current supply for the PTC resistor plate 10 is provided via the cables soldered to the contacting strips 14 and 15.

FIGS. 3 to 14 show schematically in section embodiments of the microvalves and their function.

Figure 3:
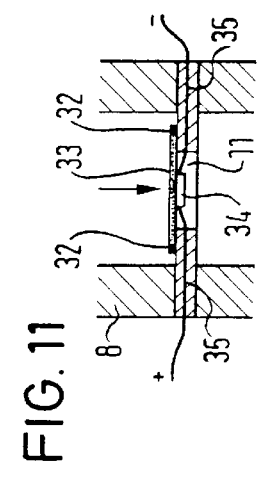
FIG. 3 and FIG. 4 show schematically the function of a disposable microvalve (closer) at rest and after electrical actuation.
Figure 4:
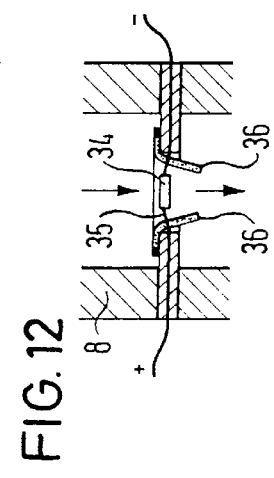

FIG. 3 shows schematically in section a valve with a closer function. Here, the thermally fusible plug 16 with its open central channel 17 is inserted in the perforation (valve aperture) of the PTC resistor plate 10. In FIG. 4, the state after valve actuation is shown. Under the effect of electrical current, the PTC resistor heats up, the material of the plug 16 fuses and closes the valve aperture as the plug 18.

Figure 5:
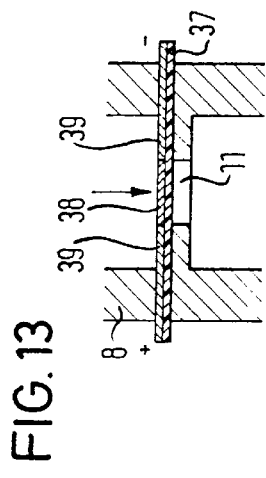
FIG. 5 and FIG. 6 show schematically the function of a disposable microvalve (opener) at rest and after electrical actuation.
Figure 6:
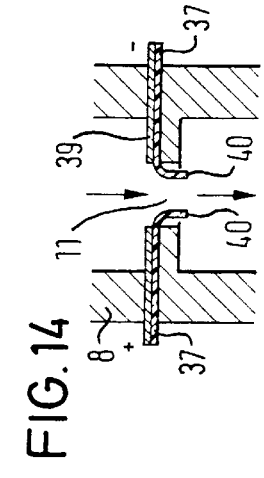

FIGS. 5 and 6 show a microvalve with an opener function.

In the embodiment shown here, in FIG. 5 a valve aperture 11 is closed in a PTC resistor by a thermally fusible plug 19. On the lower side of the PTC resistor, a thick plate 20 made from absorbing material (e.g. cellulose fibres) is provided glued on only at its edges 22 and provided with a central perforation 21. As can be seen clearly in FIG. 6, when current is applied, heating occurs with fusing of the closing plug 19 and absorption of the liquified material 24 with the opening of the channel 23.

Figure 7:
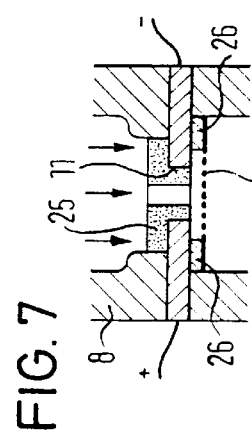
FIG. 7 and FIG. 8 show as another example the function of a disposable microvalve (closer) which uses a wax plug with an open central channel in combination with a perforated plate as the closing elements, at rest and after electrical actuation.
Figure 8:
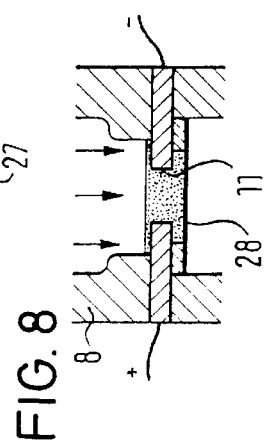
Figure 9:
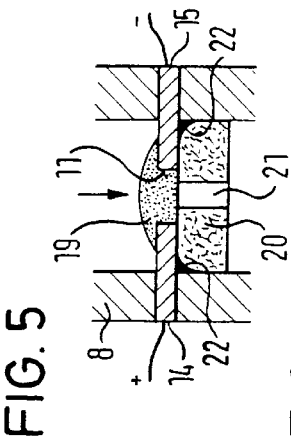
FIG. 9 and FIG. 10 show as another example a microvalve as an opener which uses only a simple wax plug as the fusible closer, at rest and after electrical actuation.
Figure 10:
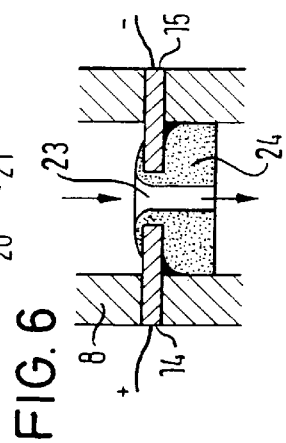

FIGS. 7 and 8 show a suitable microvalve design with a closing function at a higher pressure stress. Here, a thermally fusible plug with an open central channel 25 is inserted in the valve aperture 11 of the PTC resistor plate 10. On the lower side of the PTC resistor plate a thin screening (mesh, perforation, pore fleece) plate 27 in metal or plastic is additionally applied (glued). After heating under the application of current, you can see in FIG. 8 the valve aperture 11 closed like the fine perforation of the screening plate by thermally fusible material. Another embodiment (FIGS. 9 and 10) shows how the valve aperture 11 under pressure 31, closed only by a wax plug 30 leads after heating of the PTC resistor under the application of current to a liquification of the plug with a blowing free of the valve aperture of wax 32, see FIG. 10.

Figure 11:
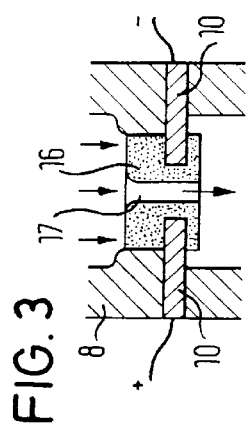
FIG. 11 and FIG. 12 show as an example a microvalve as an opener which uses as its closing element an easily fusible membrane with an SMD resistor or resistance wire being forced against it, at rest and after electrical actuation.
Figure 12:
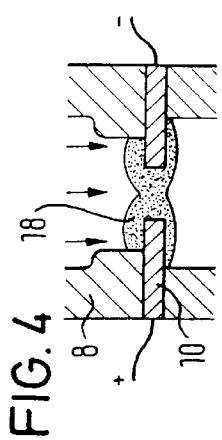

FIGS. 11 and 12 show additionally a realisation of microvalves by means of glued (adhesive rim 32), thermally fusible plastic films or wax membranes 33 which close the valve aperture 11 in a gas tight manner and on which an electrically heatable resistor 34 (e.g. SMD resistor, resistance wire) has an effect in the region of the valve aperture 11.

FIG. 12 shows after current application the resistor 34 hanging at its wire ends 35 in the valve aperture 11 and the remains of the opened valve membrane 36. FIG. 13 and FIG. 14 finally show a microvalve version (opener) where the electrical resistance element 38 is applied directly to the easily fusible valve closing membrane 37 together with the electrical connection leads 39 (e.g. by means of vapour deposition or printing on). FIG. 14 shows the state after valve actuation. The closing film 37 is torn open in the region of the valve aperture 11 and shows residues 40 of the same folded open.

FIG. 15 then shows schematically as an application example for these microvalves from the area of medical technology one programmable infusion medication application apparatus designed for outpatient and ward treatment. The core of this application apparatus is a disposable cartridge 41 connected via the programmable, electronic control current supply apparatus 42. Connected to this disposable cartridge 41 via Luer lock connections 43 are both gravity infusion apparatuses 44, 45, 46, each comprising an infusion container, drip chamber and drain system with drip regulation and one-way valve and hypodermic syringes (medication storage containers) 47, 48, 49 under spring pressure 50 (with the exception of apparatus 46) by means of the integrated electrical microvalves (V1 to V5). Via the gravity infusion apparatus 46, the cartridge 41, the patient infusion lead 51 connected to this and the butterfly hollow needle 52 fixed in the patient's vein 53 are slowly and continuously flooded with infusion solution. By opening the microvalves V1 to V5 according to an individually preselected program by the electronic control current supply apparatus 42, now the desired infusions 44, 45 and medication 47 to 49 can be fully automatically dispensed to the patient. Naturally, the low-cost disposable microvalves described can also be used advantageously, for example, in portable chemical microanalysis units.

Now the description of the design of the infusion medication application apparatus from FIG. 15 is given by means of FIG. 16 to FIG. 29.

Description of the infusion medication application apparatus

As shown in FIG. 16, this consists of the Parts A, B, C and D. Sterile infusion fluid is supplied via an infusion hose 54 with integrated one-way valve 55, as shown by an arrow, to Part A, the valve metering distribution cartridge, in a conventional manner making use of gravity, e.g. from bottles or bags hung on, and dispensed (in the direction of the arrow) to the patient via the supplying hose with subsequent bacteria venting filter 56. Additionally, medication solutions from containers under pressure, e.g. bags or syringes, can be fed into Part A via infusion leads with Luerlock connectors 61, 62 via the Luer lock connectors with subsequent particle filters 57, 58, 59, 60. As can be seen in FIG. 16, Part B, the syringe holding apparatus with spring transmission elements, is flanged to Part A with the aid of its connection plate 63 and secured with interlocking element 64. The two 10 ml syringes 65, 66 inserted in the holders are interlocked with their Luer lock connectors (not visible in the Figure) with two of the four Luer lock connectors additionally fitted to Part A on this side. Their syringe plungers 67, 68 with the associated syringe rods 69, 70 are pushed into the syringe barrels via pressure plates 72, 73 swivelled on drawbars 71. The drawbar 71 drawn with associated pressure plate 74 is also intended to demonstrate the rest position of the integrated spring transmission element. The translucent, cylindrical protective lid 75 (Part D) interlocked on Part B serves as a contact protection for drive elements and syringe strikers.

The threaded bolts 76, fitted to the front and rear sides of Part C, the programmable, electrical/electronic control current power pack, can serve as mounting elements for hangers.

FIG. 17 shows in perspective view Part B, the syringe holding apparatus with integrated spring transmission elements.

As can clearly be seen, the syringe holding apparatus comprises a cylindrical body 77 with flanged connection plate 63, which body is preferably made of light plastic. Introduced into this cylindrical body are 4 cylindrical longitudinal grooves 78 as holders for the syringes, a large central borehole 79 as a weight reduction and 4 boreholes 80 to accept the spring transmission elements. For reasons of clarity, only two spring transmissions are drawn (in the loaded and unloaded states). The spring transmission shown in simplified, loaded form on the left of the drawing, comprises the tension spring 81 anchored to the bottom of the borehole 80 at maximum load which is surrounded at its upper part by the guidance rod=drawbar 71 which swivelbears the pressure plate 82. This pressure plate pushes the abutting syringe rod and plunger of the inserted syringe into the shown direction of the arrow 83. On the right of the drawing, the spring transmission is shown in an unloaded position (rest position) with its pressure plate 84.

FIG. 18 shows in perspective view Part A, the valve metering distribution cartridge with electrical connection plug 85. In series after interlocking perforation 86, the connecting hoses 54 and 56 and Luer lock connections 87, 88, 89, 90 are connected particle filters 91 in each case which protect the metering capillaries of the metering distributor connected in series against obstruction. On the lower side of Part A, 4 Luer lock connections 92, 93, 94, 95 (only 92, 93 are visible) are also provided, each at an angle of 45 degrees to those of the upper side. Particle filters 91 are fitted in series to each of these Luer lock connectors, too.

FIG. 19 shows as a possible supplementary Part B a second syringe holding apparatus with connecting plate 96 and interlocking element 97, but not yet fitted with spring transmission elements. It is also clearly visible how, in assembly, each of the Luer lock connections 92 and 93 and the not visible connections 94 and 95 take up position in the syringe holding grooves 98 and 99 or 100 and 101 respectively.

FIGS. 20 to 26 show in perspective view, one after the other, the components from which Part A is assembled.

Figure 20:
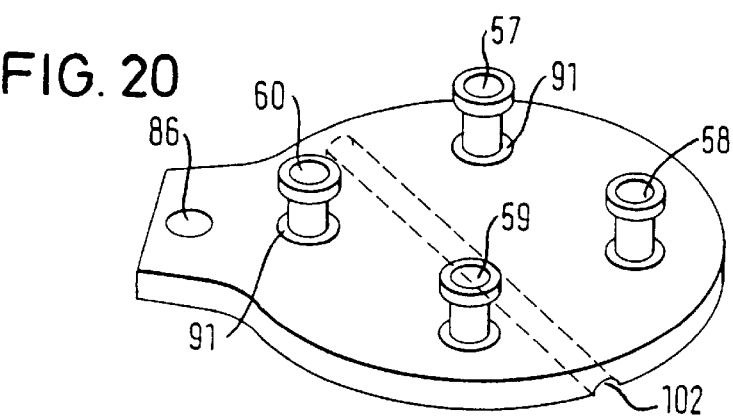
Figure 21:
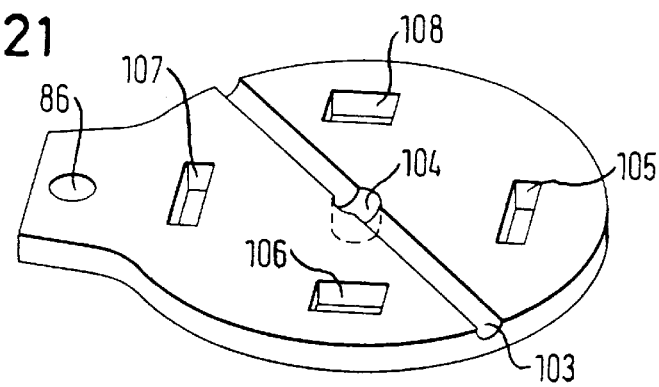

FIG. 20 shows the round top plate with protrusion from Part A with interlocking perforation 86, the upper part of the channel 102 and the 4 Luer lock connections 75, 58, 59, 60, which each have the particle filters 91 in series after them. FIG. 21 the following round plate with protrusion, interlocking perforation 86, the lower part of the channel 103 with central channel 104, the 4 rectangular cut-outs 105, 106, 107, 108 for the microvalves shown in FIG. 7.

Figure 22:
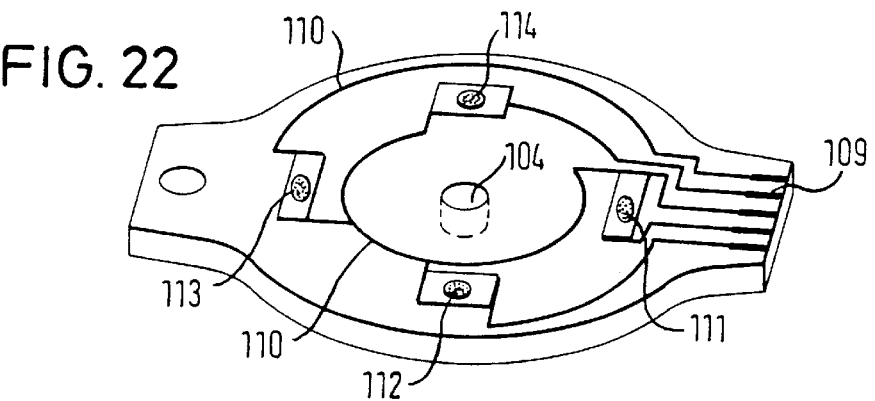

FIG. 22 shows the first valve plate with the interlock protrusion with perforation 86 and the protrusion 109 transformed into an electric plug by means of the printed electrical contacts. In addition, this plate possesses a central channel 104, four rectangular cut-outs densely covered with electrical microvalves 111, 112, 113, 114 and printed electrical conductors 110 which connect the valves.

Figure 23:
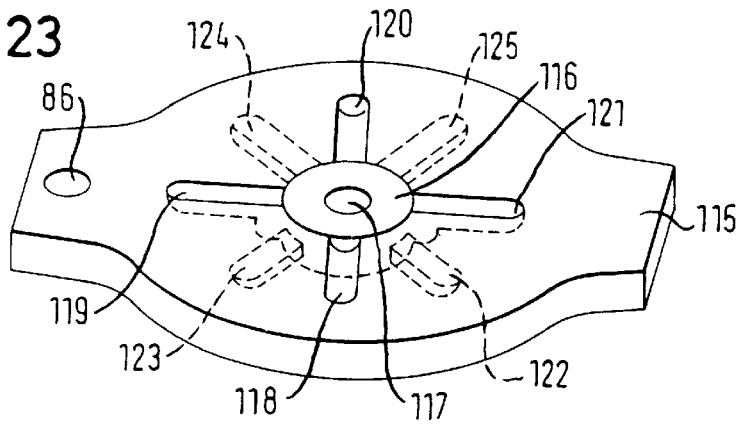

FIG. 23 shows the micro-metering distributor plate. It possesses two protrusions, the one provided with an interlock perforation 86, the other designed as an abutment 115 for the electric plug 109 (see FIG. 7). In the centre of the disc is located the metering apparatus 116 with the central channel 117 and its 2×4 supply channels 118, 119, 120, 121 and 122, 123, 124, 125 respectively each in two planes and angled through 45 degrees to one another and each open towards the upper or lower sides respectively.

Figure 24:
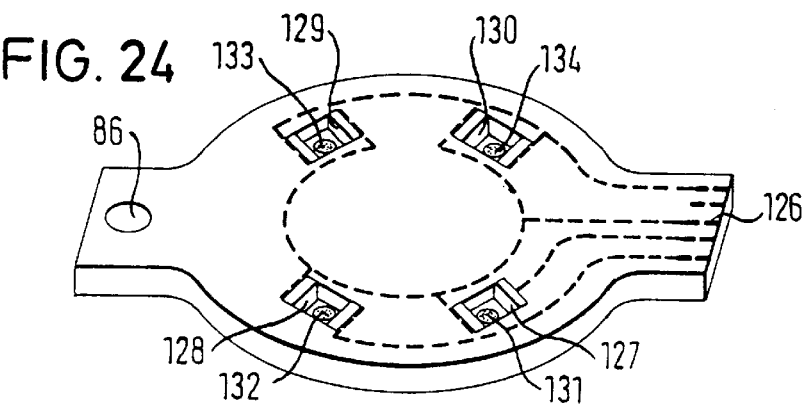

FIG. 24 shows the second valve plate with the interlock protrusion with perforation 86 and the protrusion 126 transformed into an electric plug by means of the electrical contacts printed on the lower side (shown by broken lines). In addition, this plate possesses four rectangular apertures 127–130 whose bottoms are formed in each case by four densely applied microvalves 131–134. These microvalves are connected to one other and to the electric plug 126 by means of printed conductors (shown in broken lines) applied to the lower side of the plate.

Figure 25:
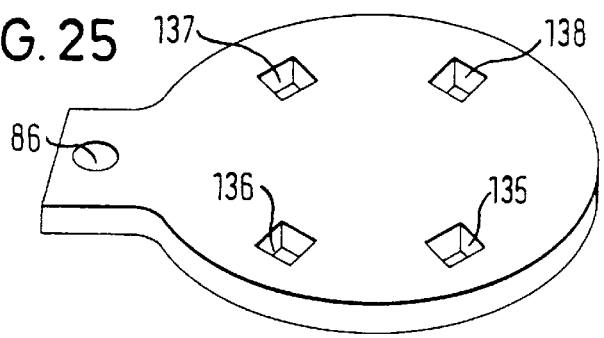
Figure 26:
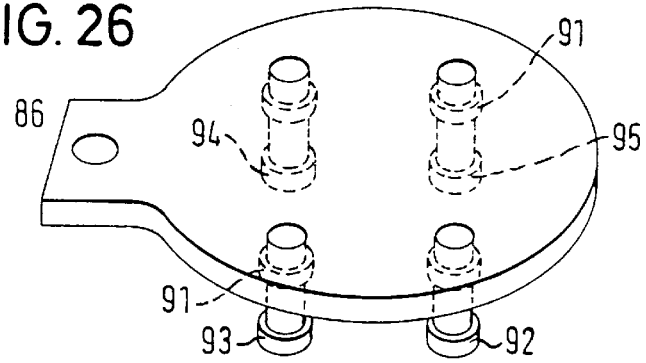

FIG. 25 shows a round plate with protrusion and interlocking perforation 86 and four rectangular cut-outs 135–138 for the four microvalves 131–134.

FIG. 26 again shows a round plate with protrusion and interlocking perforation 86 which plate possesses on its lower side four Luer lock connections 92, 93, 94, 95 with in-series particle filters 91 in each case.

FIG. 27 shows the plane top plate 139 of the metering apparatus with central channel 117 and FIG. 28 the associated plane bottom plate 140 with the eight dispensing grooves 142 which flow into the central channel 117 and which are each extended at their beginnings 141. By assembling these two plates 139 and 140, the metering apparatus 116 is created.

FIG. 29 shows in section Part A (section plane I . . . I, see FIG. 3). As can be see, Part A is assembled from seven layers corresponding to the representations in FIGS. 20 to 26. Corresponding to section plane I . . . I, there are located in the upper two layers, see FIG. 20 and FIG. 21, the upper part 102 and the lower part 103 of the channel 143 in whose ends the infusion hose 54 and the drainage hose 56 are respectively glued and which is connected via the channel 104 (see FIG. 21 and FIG. 2) with the central channel 117, the metering apparatus, which is formed from the top plate 139 and the bottom plate 140.

As can be seen, this metering apparatus is supplied with infusion medication solution via the Luer lock connector 93, a valve antechamber formed by the cut-out 136, the microvalve 132 with its aperture 144, a chamber formed in series by the cut-out 128 and the distribution channel 123. This infusion medication solution flows through the extended beginning part 141 of the dispensing groove (capillary) 142 to the central channel 117 and from there, as described, 104, 143 finally into the drainage hose 56. When the closed (closure 145) microvalve 134 is electrically opened, infusion solution can also flow via Luer lock connector 95 via its valve aperture 144, the chamber formed in series by the cut-out 130 and distribution channel 125 to the dispensing apparatus and its associated dispensing capillary 142 and from there via its central channel 117 on into the channel 143 and drainage hose 56.

Function of the infusion medication application apparatus

As FIG. 16 shows, Part A, the disposable cartridge, is inserted after removal from its sterile packaging into the programmable control current power pack C (state of the art) with its electric plug 126. As an example, with a patient fitted with a venous catheter, four types of medication should be dispensed at different, exactly defined times in addition to two short infusions and one permanent infusion. The implementation of this therapy requires in accordance with the current standards of hospitals two programmable infusion pumps for the short infusions in addition to a doctor or a nurse who have to inject the medication at the desired times by hand.

When the new infusion medication application apparatus is used, only multiple use Part B (see FIG. 1) has to be connected to Part A, the four dissolved medicines drawn into commercial 10 ml syringes, without any air where possible, and then the syringes interlocked with the Luer lock connectors of Part A after their insertion into the groove-like holders of Part B. Now, each of the drawbars 71 with the pressure plates 72, 74 for the syringe rods are manually drawn out so that the tension springs 81 are loaded and the syringe contents put under pressure. Just as easily, small containers, for example, under spring or hydrostatic pressure, for small infusions can be connected to Part A (Luer lock connections 57–60) via one-way valves for short infusion. The permanent infusion can be performed via connection 54, the connection to the patient via connection 56 (with bacteria venting filter). The pre-programming of Part C, the electro-electronic control current power pack (small rechargeable battery operation) can be effected and also documented very simply with a standard personal computer connected by means of an infrared interface prior to or even subsequent to the beginning of the infusion therapy using a simple program.

Short infusions or also medication applications can now be performed fully automatically at the desired times by the respective opening of the associated microvalves and dispensing apparatuses of the disposable cartridge (Part A). By means of supplementary Part E, as required, four further medication syringes can also be connected. Just as easily, during the pre-programming by the physician, any additional or premature medication dispensing into the infusion system controllable by the patient which is desired can be implemented. The interlockable protective lid D shown in FIG. 1 further allows a wide protection against medication abuse.

What is claimed is:

1. A microvalve for disposable use comprising:
   a casing;
   at least one valve seat formed in the casing;
   a closing element disposed in the at least one valve seat, the closing element being fusible under thermal application for opening or closing of the microvalve; and
   at least one electrical heating element thermally coupled to the closing element for supplying heat to the closing element;
   wherein, upon fusing, a central portion of the closing element melts open for opening the microvalve or the closing element melts into a central portion for closing the microvalve.

2. A microvalve in accordance with claim 1, further comprising a diaphragm located at the valve seat.

3. A microvalve in accordance with claim 2 wherein the diaphragm is selected from the group consisting of a sieve, a perforated member, a grating and a porous plate and wherein the diaphragm is made from materials selected from the group consisting of metal or plastic.

4. A microvalve in accordance with claim 2, wherein the diaphragm is made of a fiber felt which contains fine capillaries.

5. A microvalve in accordance with claim 2, wherein the diaphragm is made of cellulose which contains fine capillaries.

6. A microvalve in accordance with claim 1, wherein the closing element is selected from the group consisting of a film, a plate and a plug which is made from at least one selected from the group consisting of easily fusible plastics and waxes.

7. A microvalve in accordance with claim 1, wherein the electrical heating element is formed as an active resistance which is printed or vapor deposited as a PTC resistor and/or a heating wire directly on the closing element.

8. A microvalve in accordance with claim 1, wherein the closing element is comprised of electrically conducting material.

9. A microvalve in accordance with claim 1, further comprising inlet and outlet channels formed in the casing, wherein the electrical heating element is glued or cast into the casing such that the electrical heating element separates the inlet and outlet channels in a gas-tight manner.

10. A microvalve in accordance with claim 1 wherein the electrical heating element is actuatable by such a high current impulse that vapor bubbles are formed when liquid is used in the region of the heating element.

11. A microvalve in accordance with claim 1, further comprising an air-filled chamber disposed adjacent to the electrical heating element.

12. A microvalve in accordance with claim 1, wherein the closing element is a closing film on which the electrical heating is applied directly.

13. A microvalve in accordance with claim 1 wherein the electrical heating element is subjected to such a high electrical load during a valve triggering procedure that a resistance structure of the heating element is destroyed, thereby indicating adequate valve function.

14. A microvalve in accordance with claim 1, further comprising a central channel formed in the closing element.

15. A microvalve for disposable use comprising:
   a casing;
   at least one valve seat formed in the casing;
   a closing element disposed in the at least one valve seat, the closing element being fusible under thermal application for opening or closing of the microvalve; and
   at least one electrical heating element comprising a perforated resistance plate, wherein the closing element is applied to the perforated resistance plate by at least one of pressing, gluing, welding and fusing under thermal application;
   wherein, upon fusing, a central portion of the closing element melts open for opening the microvalve or the closing element melts into a central portion for closing the microvalve.

16. A microvalve for disposable use comprising:
   a casing;
   at least one valve seat formed in the casing;
   a closing element disposed in the at least one valve seat, the closing element being fusible under thermal application for opening or closing of the microvalve; and
   at least one electrical heating element thermally coupled to the closing element, wherein the electrical heating element comprises a thermostatically controlled, perforated PTC (Positive Temperature Coefficient) resistor.

* * * * *